US00PP24333P3

(12) United States Plant Patent
Vitten et al.

(10) Patent No.: US PP24,333 P3
(45) Date of Patent: Mar. 25, 2014

(54) STRAWBERRY PLANT NAMED 'DRISSTRAWTHIRTYTWO'

(50) Latin Name: *Fragaria×ananasssa*
Varietal Denomination: DrisStrawThirtyTwo

(75) Inventors: Matthias D. Vitten, Aptos, CA (US); Carlos D. Fear, West Malling (GB); Bruce D. Mowrey, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 49 days.

(21) Appl. No.: 13/507,687

(22) Filed: Jul. 20, 2012

(65) Prior Publication Data

US 2014/0026266 P1 Jan. 23, 2014

(51) Int. Cl.
*A01H 5/00* (2006.01)

(52) U.S. Cl.
USPC ..... Plt./208

(58) Field of Classification Search
USPC ..... Plt./208
See application file for complete search history.

*Primary Examiner* — Annette Para

(74) *Attorney, Agent, or Firm* — Jondle Plant Sciences Division of Swanson & Bratschun, L.L.C.

(57) ABSTRACT

A new and distinct variety of strawberry plant named 'DrisStrawThirtyTwo' particularly characterized by large fruit with sweet, juicy flavor, conic shape and dark red color is disclosed.

2 Drawing Sheets

Genus and species: *Fragaria×ananassa.*
Variety denomination: 'DrisStrawThirtyTwo'.

BACKGROUND OF THE NEW PLANT

The present invention relates to a new and distinct strawberry variety designated 'DrisStrawThirtyTwo' and botanically known as *Fragaria×ananassa*. This new strawberry variety was discovered in Kent, United Kingdom in June 2007 and originated from a cross between the proprietary female parent '89J167' (unpatented) and the proprietary male parent '283M 52' (unpatented). A single plant was selected for asexual propagation via tissue culture and vegetative cuttings in Kent, United Kingdom in 2007.

'DrisStrawThirtyTwo' underwent further testing in Kent, United Kingdom for seven years (2006-2012). The present invention has been found to retain its distinctive characteristics through successive asexual propagations via stolons and tissue culture.

Plant Breeder's Rights for this variety have not been applied for. 'DrisStrawThirtyTwo' has not been made publicly available or sold more than one year prior to the filing date of this application.

SUMMARY OF THE INVENTION

The following are the most outstanding and distinguishing characteristics of this new cultivar when grown under normal horticultural practices in Kent, United Kingdom.

1. Large fruit with sweet, juicy flavor;
2. Conic shape; and
3. Dark red color.

DESCRIPTION OF THE PHOTOGRAPHS

The accompanying color photographs show typical specimens of the new variety at various stages of development. The colors shown are as true as can be reasonably obtained by conventional photographic procedures. The photographs were taken from eight to ten-month-old plants.

DESCRIPTION OF THE NEW VARIETY

Figure 1:
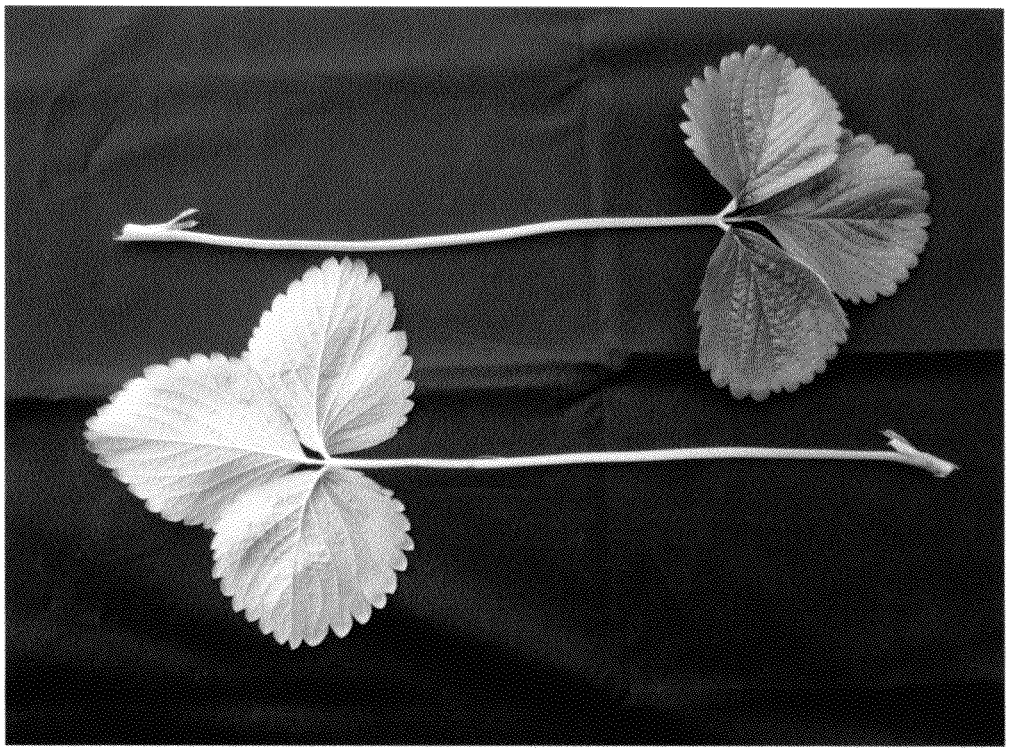
FIG. 1 shows upper and lower surfaces of the leaves of the plant with three leaflets.
Figure 2:
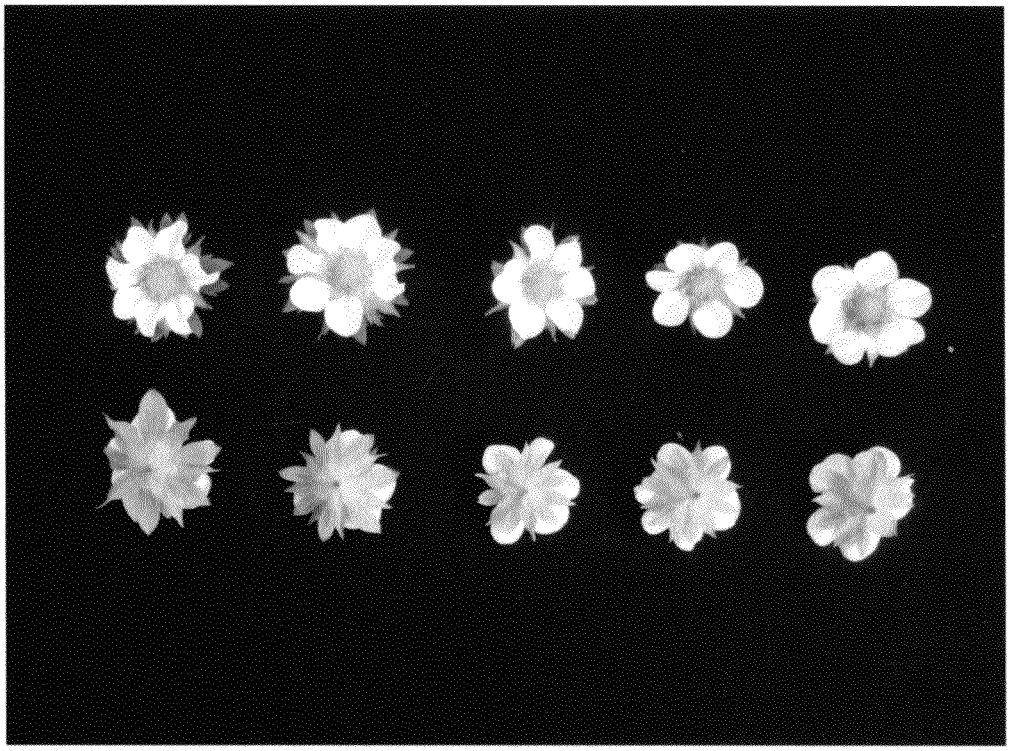
FIG. 2 shows both upper and lower surfaces of the flowers.
Figure 3:
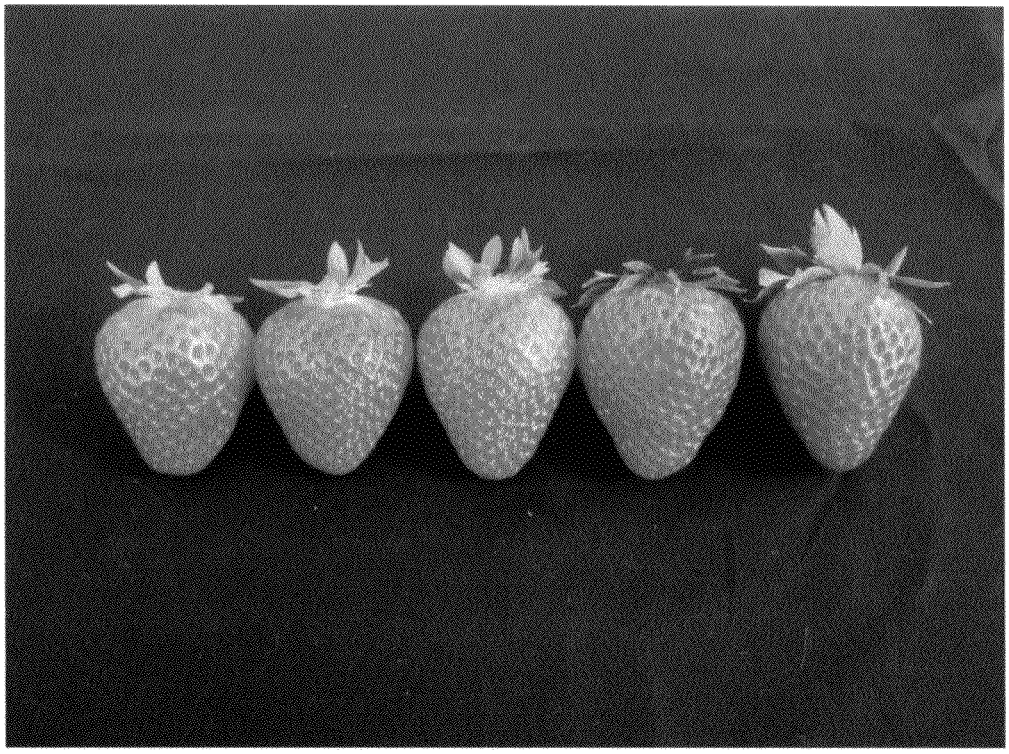
FIG. 3 shows the whole fruit.
Figure 4:
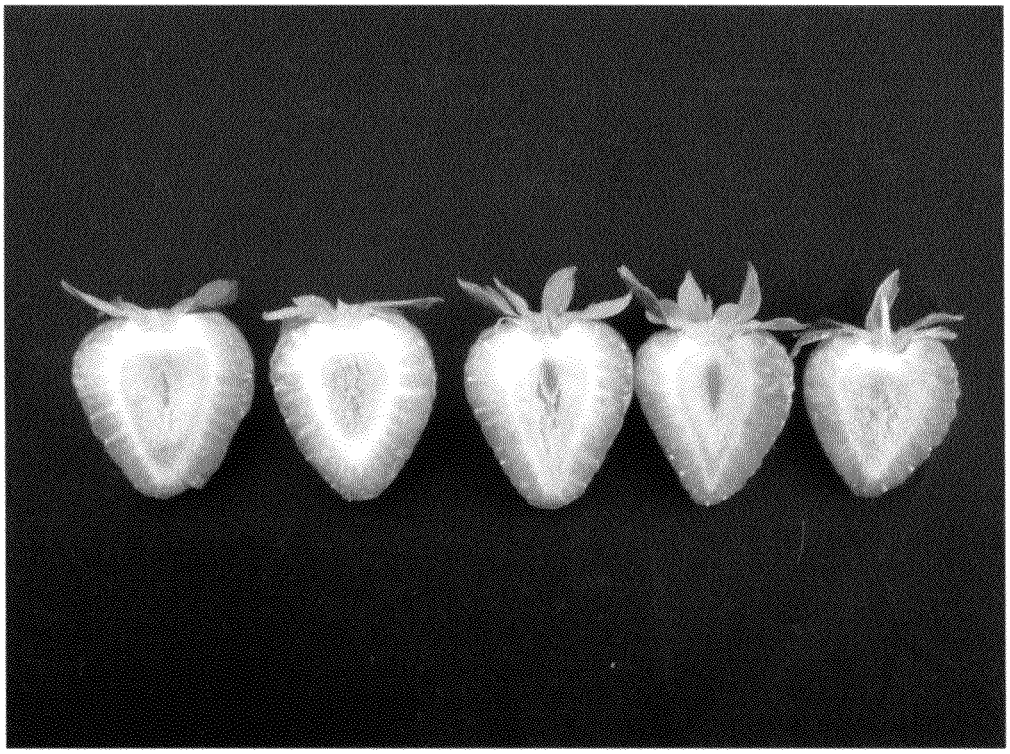
FIG. 4 shows the fruit in longitudinal cross-section.

The following detailed descriptions set forth the distinctive characteristics of 'DrisStrawThirtyTwo'. The data which define these characteristics is based on observations taken in Kent, United Kingdom from 2006 to 2012. This description is in accordance with UPOV terminology. Color designations, color descriptions, and other phenotypical descriptions may deviate from the stated values and descriptions depending upon variation in environmental, seasonal, climatic, and cultural conditions. 'DrisStrawThirtyTwo' has not been observed under all possible environmental conditions. The botanical description of 'DrisStrawThirtyTwo' was taken from eight to ten-month-old plants. Color references are primarily to The R.H.S. Colour Chart of The Royal Horticultural Society of London (R.H.S.) (2007 edition). Descriptive terminology follows the *Plant Identification Terminology, An Illustrated Glossary,* $2^{nd}$ edition by James G. Harris and Melinda Woolf Harris, unless where otherwise defined.

DETAILED BOTANICAL DESCRIPTION OF THE PLANT

Classification:

*Species.*—*Fragaria×ananassa.*
*Common name.*—Strawberry.
*Denomination.*—'DrisStrawThirtyTwo'.

Parentage:
*Female parent*.—The proprietary variety '89J167' (unpatented).
*Male parent*.—The proprietary variety '283M 52' (unpatented).
Plant:
*Height*.—42.0 cm.
*Diameter*.—50.4 cm.
*Number of crowns/plant*.—5.
*Habit*.—Upright.
*Density of individual plant*.—Medium.
*Vigor* (*health and hardiness of plant*).—Strong.
Terminal leaflets:
*Size*.—Medium. Length: 8.27 cm. Width: 8.68 cm. Length/width ratio: 1.0.
*Number of teeth/terminal leaflet*.—19.
*Shape of teeth*.—Obtuse — serrate to crenate.
*Color*.—Upper surface: RHS N137A (Dark green). Lower surface: RHS 138B (Medium green).
*Shape in cross section*.—Slightly concave.
*Blistering*.—Weak.
*Glossiness*.—Medium.
*Number of leaflets*.—Three only.
*Shape*.—Oval.
*Base shape*.—Obtuse.
*Apex descriptor*.—Rounded.
*Variegation*.—Absent.
*Margin*.—Serrate.
*Margin profile*.—Revolute.
Petiole:
*Length*.—Long; 3.41 cm.
*Diameter*.—6.19 mm.
*Pubescence*.—Sparse.
*Pose of hairs*.—Upwards.
*Color*.—RHS 144C (Light yellow-green).
*Bract frequency*.—0.
Petiolule:
*Length*.—8.70 mm.
*Diameter*.—3.19 mm.
*Color*.—RHS 144D (Light yellow-green).
Stipule:
*Length*.—3.1 cm.
*Width*.—12.84 mm.
*Pubescence*.—Sparse.
*Stipule anthocyanin coloration*.—Weak; RHS 50B (Medium red).
Stolon:
*Number*.—Many.
*Average number of daughter plants per plant*.—25.
*Stolon anthocyanin*.—Absent or very weak; RHS 145A (Light yellow-green).
*Thickness*.—Medium.
*Pubescence*.—Sparse.
Inflorescence:
*Position relative to foliage*.—Level.
*Number of flowers*.—Many.
*Time of flowering* (*50% of plants at first flower*).—Medium.
*Flower size*.—Medium.
*Diameter*.—37.86 mm.
*Petals*.—Shape: Orbicular. Apex: Rounded. Base: Convex. Margin: Entire. Spacing: Touching. Length: 16.09 mm. Width: 17.25 mm. Length/width ratio: 0.9 (As long as broad). Petal number per flower: 6. Color (upper surface): RHS 155C (White).
*Calyx*.—Diameter: 38.46 mm. Diameter relative to corolla: Smaller. Inner calyx diameter relative to outer: Same size. Insertion of calyx: Level. Pose of calyx segments: Spreading to outwards. Size of calyx in relation to fruit: Slightly smaller. Adherence of calyx: Medium.
*Sepal*.—Shape: Elliptical. Apex: Truncate. Margin: Entire. Length: 15.92 mm. Width: 7.50 mm. Sepal number per flower: 6.
*Receptacle color*.—RHS 153C (Medium yellow-green).
*Stamen*.—Present. Anther color: RHS 12A (Medium yellow).
*Pedicel*.—Attitude of hairs: Slightly upwards.
Fruiting truss:
*Length*.—Long; 31.3 cm.
*Diameter at base of truss*.—6.36 mm.
*Number of berries per fruiting truss*.—5.
*Attitude at first picking*.—Erect.
*Color at base of truss*.—RHS 143C (Medium green).
Fruit:
*Relative fruit size*.—Large.
*Length*.—47.39 mm.
*Width*.—40.91 mm.
*Length/width ratio*.—1.2.
*Fruit hollow length*.—25.90 mm.
*Fruit hollow width*.—15.72 mm.
*Fruit hollow length/width ratio*.—1.6 (Much longer than broad).
*Fruit hollow center* (*cavity*).—Medium.
*Weight* (*per individual berry*).—33.6 g.
*Predominant fruit shape*.—Conical.
*Difference in shape between primary and secondary fruits*.—None or very slight.
*Evenness of fruit surface*.—Even or very slightly uneven.
*Fruit skin color*.—RHS 46A (Dark red).
*Evenness of fruit color*.—Strongly uneven.
*Fruit glossiness*.—Medium.
*Achenes*.—Insertion of achenes: Level with surface. Coloration (sunward side of berry): RHS 153A (Medium yellow-green). Coloration (shaded side of berry): RHS N172B (Medium greyed-orange). Number per berry: 279. Weight (weight of achenes divided by total # seed): 0.006 g. Width of band without achenes: Absent or very narrow.
*Firmness of flesh*(when fully ripe).—Firm.
*Color of flesh* (*excluding core*).—RHS 44C (Medium red).
*Color of core*.—RHS 32B (Medium orange-red).
*Evenness of flesh color*.—Slightly uneven.
*Distribution of flesh color*.—Marginal and central.
*Sweetness*.—Strong.
*Acidity*.—Weak.
*Texture when tasted*.—Fine.
*Type of bearing*.—Not everbearing — not remontant.
*Grams of fruit/plant*.—600.0-800.0 g.
*Harvest interval*.—Late May to early June.
*Harvest maturity*.—Mid-season.
Disease and pest resistance:
*Botrytis fruit rot*.—Moderately resistant.
*Powdery mildew*.—Resistant.
*Verticillium wilt*.—Moderately resistant.

COMPARISON WITH COMMERCIAL VARIETY

When 'DrisStrawThirtyTwo' is compared to the commercial variety 'Sonata' (U.S. Plant Pat. No. 18,000), 'DrisStrawThirtyTwo' has leaves with an oval shape and a rounded apex, whereas 'Sonata' has leaves with a broadly ovate shape and an obtuse apex. Additionally, 'DrisStrawThirtyTwo' has a long fruiting truss length and fruit with a medium hollow center size, whereas 'Sonata' has a relatively short fruiting truss length and fruit with a weak or absent hollow center size.

We claim:

1. A new and distinct variety of strawberry plant named 'DrisStrawThirtyTwo' as described and shown herein.

* * * * *